(12) United States Patent
Havel et al.

(10) Patent No.: US 9,320,492 B2
(45) Date of Patent: Apr. 26, 2016

(54) ULTRASOUND TRANSDUCER DIRECTION CONTROL

(71) Applicant: Muffin Incorporated, West Lafayette, IN (US)

(72) Inventors: William J. Havel, West Lafayette, IN (US); Peter S. McKinnis, West Lafayette, IN (US); Yun Zhou, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 178 days.

(21) Appl. No.: 14/144,661

(22) Filed: Dec. 31, 2013

(65) Prior Publication Data

US 2014/0194744 A1    Jul. 10, 2014

Related U.S. Application Data (60) Provisional application No. 61/748,774, filed on Jan. 4, 2013.

(51) Int. Cl.
  *A61B 8/12*   (2006.01)
  *A61B 8/08*   (2006.01)
  *A61B 8/00*   (2006.01)

(52) U.S. Cl.
  CPC .............. *A61B 8/0891* (2013.01); *A61B 8/12* (2013.01); *A61B 8/445* (2013.01); *A61B 8/4461* (2013.01); *A61B 8/4466* (2013.01)

(58) Field of Classification Search
  CPC ........ A61B 8/0891; A61B 8/12; A61B 8/445; A61B 8/4461; A61B 8/4466
  See application file for complete search history.

(56) References Cited

U.S. PATENT DOCUMENTS

| | | | |
|---|---|---|---|
| 4,092,867 A | 6/1978 | Matzuk |
| 4,246,792 A | 1/1981 | Matzuk |
| 4,649,925 A | 3/1987 | Dow et al. |
| 4,756,313 A | 7/1988 | Terwilliger |
| 4,785,816 A | 11/1988 | Dow et al. |
| 4,913,155 A | 4/1990 | Dow et al. |
| 5,088,495 A | 2/1992 | Miyagawa |
| 5,329,194 A | 7/1994 | Dow et al. |
| 5,647,367 A | 7/1997 | Lum et al. |

(Continued)

FOREIGN PATENT DOCUMENTS

| | | |
|---|---|---|
| JP | 2007-083053 A | 4/2007 |
| KR | 10-2009-0115727 A | 11/2009 |

OTHER PUBLICATIONS

English Abstract for JP 2007-083053 A.

(Continued)

*Primary Examiner* — Mark Remaly
(74) *Attorney, Agent, or Firm* — Woodard, Emhardt, Moriarty, McNett & Henry LLP (57) ABSTRACT

Disclosed are embodiments of devices and methods for imaging the inside of a body part, such as a blood vessel. In particular embodiments, a catheter has a chamber within which is a transducer mounted to a pivot mechanism, a motor for turning the transducer, and a coil for providing a pivot force to the transducer. A magnet is attached to the transducer and is receptive of a torque applied by a magnetic field produced by energizing of the coil.

20 Claims, 4 Drawing Sheets

(56) References Cited

U.S. PATENT DOCUMENTS

| | | |
|---|---|---|
| 6,198,956 B1 | 3/2001 | Dunne |
| 6,551,245 B1 * | 4/2003 | Irioka et al. .................. 600/444 |
| 6,626,834 B2 | 9/2003 | Dunne et al. |
| 2002/0107447 A1 | 8/2002 | Suorsa et al. |
| 2009/0264768 A1 * | 10/2009 | Courtney et al. ............. 600/463 |
| 2012/0108980 A1 | 5/2012 | Shilling et al. |

OTHER PUBLICATIONS

English Translation for KR 10-2009-0115727 A by Total Patent, pp. 1-43, dated Apr. 24, 2014.

International Search Report and Written Opinion of PCT/US2013/076516, dated Apr. 16, 2014.

* cited by examiner

ULTRASOUND TRANSDUCER DIRECTION CONTROL

REFERENCE TO RELATED APPLICATIONS

This application claims the benefit of U.S. Provisional Patent Application No. 61/748,774, filed Jan. 4, 2013, which is hereby incorporated by reference.

FIELD OF THE DISCLOSURE

The present disclosure concerns devices and methods for ultrasound use within the human body, including devices and methods for employing ultrasound to image body areas, such as the interior of blood vessels.

BACKGROUND

Ultrasound technology has been used for therapeutic and diagnostic medical procedures, which can include providing imaging of internal portions of a body. For example, devices have been proposed for using ultrasound imaging within blood vessels to view the condition of the vessel and/or placement or condition of a device placed in the vessel. However, a number of problems with such devices remain. For example, many such devices provide at best an image of a cross section of tissue or other items of interest, i.e. a thin, disk-shaped slice of the interior of a blood vessel with a portion in the center that is not within the range of the ultrasound beam. In some other devices, the ultrasound beam is directed at a fixed angle that is not substantially perpendicular to the longitudinal axis (e.g. at 45 degrees). In this case the imaged region is static in the form of a portion of the surface of a cone, also with a center portion that is not within the range of the ultrasound beam. In either case, in order to visualize the entirety of a significant length within the body (e.g. surfaces or portions of tissue, or of devices), the device must be moved along that length, with respective images of cross sections at particular locations taken. Such movement may be inexact, and may include risks associated with blind insertion of the device through the vessel. It is also slow. Typical pull back images take on the order of 30 seconds to perform (at a speed of about 0.1 mm/s).

Three-dimensional information provides the added value that it can be used to help in navigation of devices within the vasculature and confirmation of position of the devices. In an intravascular example, catheters can be moved up and down vessels and the image data obtained via ultrasound can be combined or otherwise processed in order to create three-dimensional information. However, the catheter tip motion and angle must be known in order to produce accurate and usable data. Three-dimensional images may be acquired by one-dimensional arrays connected to a mechanical actuator, to move the arrays within the catheter or other device. Such designs are expensive and generally require more space in a device than many vessels will permit. To achieve good image quality, such array transducers must simultaneously transmit and receive on many separate channels. That condition requires many expensive and bulky coaxial cables. Fewer coaxial cables can be used, but doing so reduces the quality of the image and image frame rate.

Ultrasound devices have been proposed which include a motion of a transducer about two axes to provide three-dimensional information. However, the mechanical mechanisms that provide such movement tend to be bulky and require dimensions which are unsuitable for applications in small body areas. Additionally, the problem of providing motion to a transducer must be solved. Designs including torque cables can be problematic. Practically, a sufficiently maneuverable torque cable creates a potential for delay in the transferring of torque from one end of the cable to the other, as the cable stores and releases elastic energy, which causes the transducer assembly to rotate at a non-uniform rate even when the rotation source rotates at a uniform rate. The non-uniform rotation rate causes the resulting data or images to be distorted. These problems are magnified if two torque cables are used for two-axis movement of the transducer. In some cases, separate motors can be used to provide movement to the transducer. However, motors require additional space and can include further disadvantages such as control wires or structural components which cross the viewing window and cause a portion of an image to be blocked. Additionally, existing feedback mechanisms for controlling complex motor motion can be costly and bulky.

There remains a need for accurate and efficient application of ultrasound in three dimensions along a substantial length of a small body area, for example to provide a physician with a real-time view along that length. There also remains a need for devices that can view a medical device and one or more tissues or tissue parts simultaneously, particularly in cases in which the device and tissue(s) could not have been imaged reliably in any two-dimensional plane.

SUMMARY

Among other things, there is disclosed an apparatus and methods for providing an ultrasound beam with two controllable degrees of freedom within the body of a patient. For example, such apparatuses can include a transducer for emitting and/or receiving ultrasound signals and a motor operatively coupled with the drive shaft such that operation of the motor rotates the shaft about a rotation axis. Also included is a pivot mechanism operatively connected to the shaft such that the pivot mechanism rotates in response to rotation of the shaft. The pivot mechanism has a pivot member which is pivotable about at least one pivot axis, the pivot axis being substantially perpendicular to the rotation axis. The pivot member includes a magnetic layer and the transducer. A coil is positioned concentric to and along the rotation axis between the motor and the pivot mechanism. The coil includes a plurality of electrically conductive windings such that application of electric current to the coil creates a torque on the pivot member about the pivot axis.

The magnetic layer may include a diametric permanent magnet having a first magnetic field poles aligned substantially perpendicular to the pivot axis such that application of electric current to the coil creates a second magnetic field poles aligned substantially along the rotation axis. In this way interaction between the first and second magnetic field creates a torque on the pivot member. The magnetic layer may also have poles aligned generally parallel with the transducer viewing angle such that application of electric current to the coil creates a second magnetic field poles aligned along the rotation axis. In that way, interaction between the first and second magnetic field creates the torque on the pivot member. The coil can be positioned concentrically outward of the drive shaft.

The device can include a bias member which is positioned to apply a bias member force to the transducer and which biases the transducer to a neutral position about the pivot axis and relative to the pivot mechanism. Torque can be dependent upon the electric current to the coil such that the torque is insufficient to overcome the bias member force, in which case the bias member force returns the transducer to the neutral position. The bias member can be a conductor which is configured for carrying signals from the transducer.

Rotation of the shaft about the rotation axis and the pivoting of the pivot member about the pivot axis are separably operable at one or more frequencies or rotational speeds. In some instances, the device is operable in one or more modes in which the angular velocity of the pivot member is dependent on the angle between the ultrasound signals and the rotation axis of the shaft. For example, the device can include an operational mode such that the motor turns faster when the pivot mechanism is in a state such that the ultrasound signals are pointing in a direction closer to the rotation axis. The device can also include an operational mode such that the motor turns slower when the pivot mechanism is in a state such that the ultrasound signals are pointing in a direction further from the rotation axis.

The device can include a cylindrical sheath enclosing the motor and pivot mechanism which provides structural support for the coil. The sheath can be a catheter wall. Additionally, the device can be positioned within the catheter. The shaft can include a lumen extending therethrough. The device can also include a limit stop positioned to limit the pivotal motion of the pivot member at the either end of its pivotal range. The device can also include arms which provide a mounting for the pivot member such that the limit stop is a bar extending between the two arms. The transducer can be movable throughout a range which defines a viewing window extending from the transducer. The device can include an opaque feature within the viewing window such that the opaque feature provides angular position information about the pivot member.

The magnetic layer can be positioned parallel to the transducer and pivotable about a second pivot axis such that the magnetic layer and transducer are connected such that the transducer pivots in response to pivotal motion of the magnetic layer.

The device can include a tubular member for housing the transducer motor and pivot mechanism. The tubular member can have a distal chamber defined at least in part by a wall portion of the tubular member. The distal chamber housing can include the transducer and a medium such that the wall portion and the medium have similar ultrasound passage characteristics to the part of the body into which the tubular member is inserted, such that reflection of ultrasound at the boundary of the medium in the wall portion and at the boundary of the wall portion and the body environment is reduced to a level acceptable for imaging through the boundary.

Further forms, objects, features, aspects, benefits, advantages, and embodiments of the present disclosure will become apparent from a detailed description and drawings provided herewith.

DESCRIPTION OF THE SELECTED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. One or more embodiments are shown and described in detail, although it will be apparent to those skilled in the relevant art that some features that are less relevant may not be shown for the sake of clarity.

Referring now generally to the drawings, there are shown exemplary embodiments of a device 20 for internal ultrasound procedures. Such devices may be diagnostic or therapeutic (including interventional) in application, and include devices inserted percutaneously, subcutaneously or endoluminally into the patient. Device 20 can be used with a system which includes a console (not shown) for processing data or signals received from an ultrasound transducer. The ultrasound console can be a type which is generally used for medical ultrasonic imaging, e.g. generally including control devices usable by a physician and a graphic display which displays graphical images obtained during an ultrasound procedure. Device 20 can be used for obtaining images at various locations of a body such as a blood vessel, urethra, ureter, vagina, rectum, throat, ear, or through an artificial tract (or lumen) by percutaneous puncture, for example. The console portion can be connected to commercially-available ultrasound probes or catheters with compatible pinout, or other medical devices which are configured for endoluminal procedures. Device 20 is capable of transmitting and receiving ultrasound signals and then communicating data obtained from ultrasound signals to the console.

Figure 1:
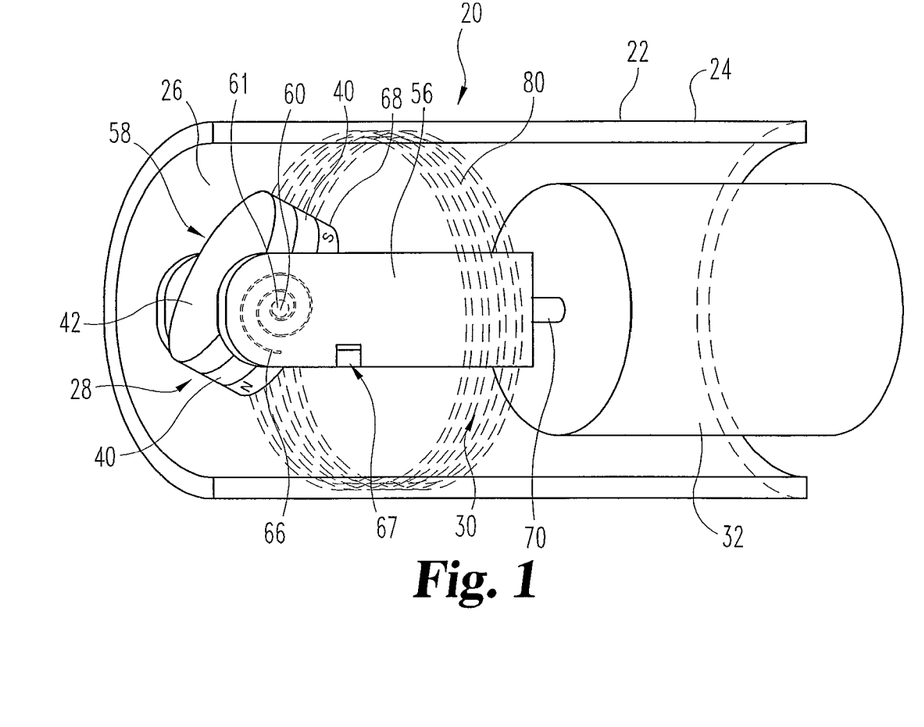
FIG. 1 is an illustrative perspective view of an embodiment of an ultrasound device having a pivot mechanism and motor.
Figure 2:
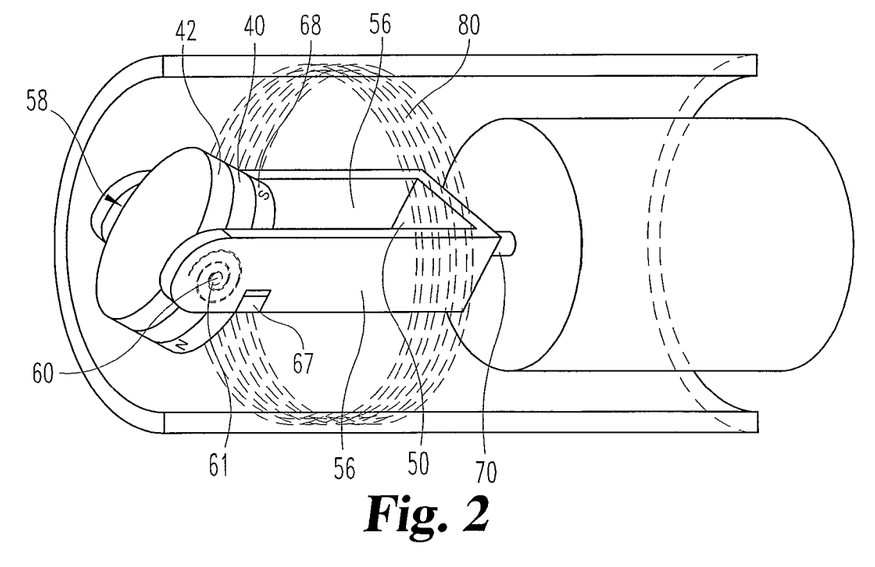
FIG. 2 is an illustrative perspective view of the embodiment of the ultrasound device of FIG. 1.

In the embodiment shown schematically in FIGS. 1 and 2, device 20 includes a catheter 22 or other flexible elongated or tubular member having a wall 24 defining an internal chamber 26, within which is included a transducer 28, a pivot mechanism 30, a motor 32, and a coil 80. Catheter 22 is sized and configured for insertion into and/or travel along bodily orifices or lumens. As will be discussed further below, pivot mechanism 30 allows transducer 28 to be turned around a longitudinal or rotation axis of device 20 as well as pivoted around a pivot axis substantially perpendicular to the longitudinal or rotation axis, allowing the direction of ultrasound emission and reception to extend forward (axially relative to the rotation axis) and laterally (radially relative to the rotation axis). In the illustrated embodiments, the rotation axis is the longitudinal axis (i.e., extending axially through catheter 22) of device 20, and the pivot axis is a lateral axis (e.g. perpendicular to the longitudinal axis). Transducer 28 in conjunction with motor 32 and pivot mechanism 30 is capable of transmitting and receiving ultrasound signals in a variety of directions or orientations which are passed along data signal communication lines between transducer 28 and the ultrasound console.

Catheter 22 in the illustrated embodiment is an elongated device of plastic or other sturdy flexible material. Catheter 22 includes a control end (i.e., proximal end) which during use is nearest to the user and an application end (i.e., distal end)

which during use is nearest to the user's point of interest. The terms "control" and "application" are used throughout this description to describe these positional orientations. Wall 24 surrounds chamber 26, which is at or near the application end of device 20 in the illustrated embodiment. The control end of wall 24 and/or catheter 22 may extend outside of the patient during use, or may attach to another piece that extends outside the patient, and may end in a handle or other operating portion for maneuvering catheter 22.

Catheter 22 has at least a portion that presents a minimal barrier to the passage of ultrasound signals so that ultrasound images of surrounding matter (e.g. tissue(s) or implant(s)) may be reasonably acquired through the barrier. Catheter 22 has a portion that is constructed of a material which is substantially echolucent (i.e., having small ultrasound attenuation, or having a small difference in acoustic impedance with the surrounding environment) when placed in the surrounding working environment, such that it acts as an acoustic window which allows passage of ultrasound signals with minimal reflection. It will be understood that only the application end of catheter 22 (e.g. wall 24) need be acoustically transparent, but more or all of catheter 22 may be made of the same material as wall 24 in some embodiments. For example, when used within a blood vessel containing body tissues and blood, it is preferable for catheter 22 to be constructed of a material which is structurally rigid and which has acoustic impedance similar to that of body fluids such as blood. Possible materials could include, for example, a polymer material such as high density polyethelene, polymethylpentene (PMP), or acrylonitrile butadiene styrene (ABS). It has been determined that in some cases the thickness of at least the portion of catheter 22 which serves as the viewing window can be approximately N/2 (where N is a positive integer) of the wavelength corresponding to the center frequency of the ultrasound signal.

Particular embodiments of catheter 22 or at least chamber 26 are cylindrical, and are sized for insertion into and passage through blood vessels, such as insertion into the femoral artery and passage through it toward the heart. Wall 24 may have a port or other feature to allow injection of fluid (e.g. saline, oils, or alcohols) into chamber 26 to give chamber 26 ultrasound characteristics similar or substantially identical to that of wall 24 and the surrounding bodily environment (e.g. the blood stream). A bearing or other sealing member can be placed between motor 32 and transducer 28 or the portion of chamber 26 containing transducer 28 and a fluid, in the illustrated embodiments.

Transducer 28 is mounted in pivot mechanism 30 to permit transducer 28 to turn around the rotation axis as well as pivot around the pivot axis. In the illustrated embodiments, pivot mechanism 30 is a two-axis gimbal or gimbal-type mounting (or yoke), having a base 50 and matching arms 56 extending from base 50. Base 50 accommodates a shaft from motor 32, so that motor 32 can turn pivot mechanism 30. A pivot member 58 is mounted to arms 56 via holes 60 in arms 56. Pivot member 58 in the illustrated embodiment is a circular shaped disk having shafts 61 that fit into holes 60 and act as an axle, so that pivot member 58 can pivot around the axis defined by shafts 61. Other gimbal structures could be used which provide pivoting (or elevational) rotational motion to the transducer, examples of which are explained in U.S. App. Ser. No. 61/713,172 (entitled "Devices and Methods for Three-Dimensional Internal Ultrasound Usage"), and incorporated herein by reference in its entirety.

One or more bias members 66 bias pivot member 58 to a particular initial resting or neutral position. In the illustrated embodiment, bias member 66 is a torsion spring connected to an arm 56 at or toward one end, and to shaft 61 or pivot member 58 at the other (e.g. by inserting an end of bias member 66 into a groove in shaft 61). The torsion spring is a helically shaped spring; although other spring types are suitable. A second bias member 66 (not shown) may be similarly attached to the other arm 56 and shaft 61 or pivot member 58. In the embodiment of FIGS. 1 and 2, in the neutral position transducer 28 is oriented substantially along the rotation axis; e.g. transducer 28 has a viewing angle which is substantially aligned with the rotation axis with pivot member 58 generally normal to the rotation axis. In other embodiments, the neutral position can be different (e.g. with the viewing angle substantially perpendicular to the rotation axis).

Pivot mechanism 30 includes one or more limit stops 67. Limit stop 67 is provided so as to limit or bound the pivot range of member 58 at both ends of the pivot range. In the embodiment of FIGS. 1 and 2, limit stop 67 is an elongated member which is mounted to and extends between arms 56. As pivot member 58 pivots through its pivoting range, it abuts limit stop 67 (e.g. a back surface or surface opposite the side of pivot member 58 having transducer 28) at each end of the pivot range. In this way, pivot member 58 is free to rotate through a range of about 180 degrees, or about 90 degrees in either direction from the neutral position until a portion of it strikes limit stop 67. In other embodiments, limit stop(s) 67 may be tabs positioned on and extending from one or both arms 56, or another suitable structure which physically limits the pivoting motion of pivot member 58. In other embodiments, limit stop 67 could be positioned to limit or bound the pivotal range of pivot member 58 to about 90 degrees, or between a position in which the viewing angle of transducer 28 is substantially parallel to the rotation axis and a position in which the viewing angle of transducer 28 is substantially perpendicular to the rotation axis.

As previously noted, in the illustrated embodiment, transducer 28 is mounted to pivot member 58. Pivot member 58 also includes a magnetic layer 68. Transducer 28 is indicated schematically in the drawings. The term "transducer" should be understood to include an assembly of two or more parts as well as a single piece. It will further be understood that "transducer" as used herein includes devices that transmit ultrasound signals (i.e., transform an electrical (RF) signal to ultrasound), receive ultrasound signals (i.e., transform ultrasound to an electrical (RF) signal), or both. If multiple transducers or pieces are provided, transmission of ultrasound may occur at one and reception at another. Transducer(s) as described herein may have one or more piezoelectric elements as respective transducers, and may operate in combination with other transducers within or outside the body. As examples, "transducer" as used herein includes a single element transducer on a rotating and pivoting member or a one-dimensional array of elements on a rotating and pivoting member.

An exemplary transducer 28 includes a body or backing 40 with at least one ultrasound element 42 attached to one side of backing 40, and one or more clamping rings. Transducer 28 can include a matching layer (not shown) attached to one side of element 42. Element 42 in this embodiment is a piezoelectric element which has the ability to convert electrical energy into sound waves and sound waves into electrical energy. The positioning of element 42 as indicated, on a side of backing 40, results in a directed ultrasound beam direction. Backing 40 may be substantially opaque to ultrasound signals, so that such signals are effectively only projected outward from element 42, e.g. to one side or in a limited angular range radially (relative to the pivot axis) from backing 40. The matching layer has acoustic impedance generally between that of element 42 and the medium surrounding transducer 28 in order to minimize mismatched acoustic impedance between transducer 28 and the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. In some examples, transducer 28 can include a linear array of elements extending along the rotation axis. Clamping rings have been determined to improve efficiency and add mechanical stability to transducer 28.

Figure 3:
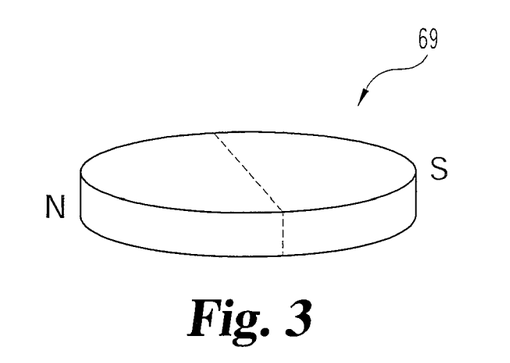
FIG. 3 is an illustrative perspective view of a magnetic layer which could be used in the FIG. 1 embodiment.

Magnetic layer 68 is positioned adjacent to or integral with backing 40 in the illustrated embodiment. Magnetic layer 68 may be a permanent magnet attached to transducer 28 adjacent to backing 40. Alternatively, magnetic layer 68 could be incorporated into a transducer housing. In other embodiments, a magnet or magnetic material may be integrated with the backing layer as a composite or other method. In the FIG. 1 embodiment, magnetic layer 68 is a permanent diametric magnet 69 (FIG. 3) having a generally cylindrical shape with the poles aligned in the radial direction, in which a pole axis running through the north and south poles is generally perpendicular to the pivot axis.

In particular embodiments, pivot member 58 is a body, base or substrate on which backing 40 of transducer 28, or transducer 28 itself, is fixed. In other embodiments, backing 40 may include shafts 61 so as to become the pivot member in pivot mechanism 30, or a separate axle may be provided with pivot mechanism 30 to which backing 40 or magnetic layer 68 is directly or indirectly fixed. Pivot mechanism 30 permits transducer 28 to turn around the rotation axis, via transmission of rotational motion from motor 32 to mechanism 30, and to turn transducer 28 about the pivot axis at the same time, via pulling or pushing force on magnetic layer 68 to move it around the pivot axis. Pivot member 58 is thus able to rotate about both the pivot axis and the rotation axis simultaneously.

Motor 32 includes a rotating shaft 70 for connecting to pivot mechanism 30. Shaft 70 can be attached to pivot mechanism 30 by interference or similar fit or by other fixed attachment (e.g. by adhesive, solder or welding) within a hole in base 50. Motor 32 is a microminiature motor in particular embodiments suitable for containment within chamber 26 of catheter 22. Examples of such microminiature motors include piezoelectric or electromagnetic motors of a size and configuration suitable for containment within chamber 26 of catheter 22. For example, a particular embodiment of motor 32 is a three-phase, coreless, brushless DC electromagnetic motor, which has few components, small size and minimal complexity. In other examples, a piezoelectric microminiature motor may be used for its advantage of not requiring a gearhead (mechanical transmission) to achieve high torque, and to eliminate problems with torque cables and rotary transformers. A microminiature motor 32 (e.g. electromagnetic or piezoelectric) has a diameter in the range of 0.3 mm to 4 mm in particular embodiments, for example approximately 2.0 mm. In some embodiments, shaft 70 is hollow (i.e., defining a lumen therethrough) and extends through the entirety of motor 32. A lumen through shaft 70 permits electrical conductors, guide wires, or other structures to pass through shaft 70.

Motor 32 may be configured to rotate shaft 70 continuously in a single rotational direction. In such embodiments, pivot mechanism 30 and transducer 28 are rotated around the rotation axis of shaft 70 in that single rotational direction. One or more of the back EMF, the ultrasound signal emitted and/or received by transducer 28, and motor saliency can be used as a feedback mechanism to precisely control the rotational position of motor 32 (and transducer 28 rotated by it) relative to the rest of device 20, ensuring proper registration of images obtained through transducer 28. Registration can be accomplished via methods and structures discussed in U.S. Application Ser. No. 61/713,142, entitled "Feedback/Registration Mechanism for Ultrasound Devices," which is incorporated by reference herein in its entirety. Motor 32 may alternatively be configured to run in a reciprocating motion, with shaft 70 switching between rotation in a first rotary direction (e.g. for a predetermined time, arc or number of turns) and rotation in a second, opposite, rotary direction (e.g. for a predetermined time, arc or number of turns). Methods and structures relating to a reciprocating motor are discussed in U.S. Application Ser. No. 61/713,135, entitled "Reciprocating Internal Ultrasound Transducer Assembly," which is incorporated by reference herein in its entirety.

Coil 80 is a conductor which is wrapped or coiled multiple times about the rotation axis. In other embodiments, coil 80 is drive coil or helical wire. In the embodiment of FIGS. 1 and 2, coil 80 is positioned in the axial direction (relative to the rotation axis) between motor 32 and transducer 28. Coil 80 is positioned adjacent to wall 24 of catheter 22. In some embodiments, coil 80 can be positioned within chamber 26 and positioned adjacent to or abutting the inside surface of wall 24. In other embodiments, coil 80 can be positioned adjacent to or abutting the outside surface of wall 24. In other embodiments, coil 80 can be integrated into wall 24 of catheter 22. In still other embodiments, coil 80 can be positioned about a tubular sheath (not shown) which is positioned within catheter 22 and surrounds at least a portion of pivot mechanism 30. In this way, catheter 22 or a sheath provide structural support for coil 80. In other embodiments, coil 80 can be positioned closer to motor 32 or closer to transducer 28.

Coil 80 has multiple windings which are positioned concentric to the rotation axis. Coil 80 has at least one end which is connected to a power source (not shown) as by a conductor leading to or toward the operating end of device 20. The power source can be positioned within or without catheter 22 (e.g. integrated with the console). The power source applies an electric current to coil 80. In this way, coil 80 is positioned such that energizing coil 80 creates a magnetic field with poles aligned substantially with the rotation axis.

In the FIG. 1 embodiment, magnetic layer 68 has poles which are symmetrically arranged perpendicularly about the pivot axis. Energizing coil 80 creates a magnetic field with poles aligned with the rotation axis. A magnetic field produced by coil 80 will have a pole (e.g. north) closest to pivot member 58 which attracts the opposite pole (e.g. south) of magnetic layer 68. The force of attraction between the two poles applies a torque to pivot member 58. The magnitude of the torque can be varied by altering the magnitude of the current applied to coil 80, and the direction of the torque can be changed by reversing the direction of the current and thus the polarity of the magnetic field produced by coil 80. When the torque is large enough to overcome the spring force of bias members 66, pivot member 58 rotates about the pivot axis from the neutral position. Limit stop(s) 67 stops the pivotal motion of pivot member 58 at the end of its pivotal range. As noted, the current applied to coil 80 can be varied in order to control the torque and therefore the angular velocity of pivot member 58. When pivot member 58 is at the end of its pivotal range, the current applied to coil 80 can be reduced or eliminated so that the spring force of bias members 66 overcome the torque of the magnetic fields in order to return pivot member 58 to the neutral position. Alternatively, the current may be reversed to create an opposite magnetic field which creates a torque from the repelling magnetic fields which works in conjunction with the spring force from bias members 66 to return pivot member 58 to or toward the resting position. In some embodiments, an alternating current can be applied to coil 80 to achieve reciprocating pivotal motion of pivot member 58.

In some embodiments, one or more acoustically opaque or attenuating features may be placed in the viewing window such that the ultrasound field crosses the opaque feature at one or both ends of the pivoting range of transducer 28. Limit stop(s) 67 may be positioned and/or configured such that transducer 28 stops at a moment when the ultrasound field crosses the acoustically opaque feature. The acoustically opaque feature may be added to or integrated with a catheter 22, examples of which are incorporated by reference above. In some embodiments, the bias members 66 can be omitted in which case a feedback sensor can be used to determine the pivot angle of transducer 28.

Transducer 28 is electronically connected to a power source and to an imaging system via signal carriers as noted previously. Bias members 66, if of conductive material, can be linked to transducer 28 and/or the console or power source to carry electrical signals to and/or from transducer 28. In particular embodiments, bias members 66 provide a conduction path from transducer 28 to conductors positioned along arms 56. Alternative to or in conjunction with bias members 66, other signal carriers could be positioned to carry a signal from transducer 28 toward the console side of device 20. Other examples of signal carriers include conductors (e.g. wires or cables) along wall 24, through a central lumen of a motor shaft, via slip ring connections, and/or via metallic film(s) along wall 24. Examples are discussed and shown in U.S. Application Ser. No. 61/714,275 (entitled "Internal Transducer Assembly with Slip Ring"), which is incorporated by reference herein in its entirety.

A portion of chamber 26 immediately surrounding transducer 28 extending towards the application end of catheter 22 can be completely filled with a fluid or other substance having acoustic impedance similar to that of blood or tissue, such as saline, oils (e.g. mineral oil or castor oil), or mixed alcohol. A seal, bearing, or other structure is positioned adjacent to shaft 70 to provide a fluid seal between motor 32 and the chamber surrounding transducer 28. The substance should minimize friction acting against transducer 28 during rotation. In this way, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image. The fluid can be added to device 20 during manufacture, or alternatively could be added prior to use. When the transducer is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port (not shown) may be positioned or creatable within the catheter or through the catheter wall to allow access for adding a fluid. In that case a corrosive fluid may be added at the time of deployment of device 20. Corrosive fluids such as water, saline, and alcohol typically have more favorable combinations of bio-compatibility, acoustic transparency and viscosity.

An example of using device 20 in the context of IVUS will now be given. As previously noted, it will be understood that devices as disclosed herein may be used in other types of internal procedures as well.

Device 20 is prepared (e.g. by injecting a fluid into chamber 26, if not already present) and inserted into the body of a patient and maneuvered to a desired location, e.g. in a particular blood vessel. Transducer 28 may be operated during travel to the desired location, as transducer 28 has a forward neutral position and can be pivoted through use of coil 80. Throughout placement and at a desired imaging location, motor 32 can be operated to turn transducer around the rotation axis to provide images of tissue(s) or other matter around device 20. Coil 80 can be energized in order to pivot transducer 28 about the pivot axis to shift the ultrasound field forward and/or laterally. Correspondingly, transducer 28 rotates about one or both the rotation axis and the pivot axis. In this way, device 20 provides an ultrasound signal sweep or field that not only turns around the rotation axis of device 20 but also around the pivot axis in order to look forward and/or laterally of a particular position of transducer 28.

When an ultrasound signal is transmitted, the ultrasound signal passes across wall 24 of catheter 22 until it encounters an acoustic impedance boundary (e.g. body tissue, plaque, medical implant, or other material which has acoustic impedance sufficiently different from bodily fluids or other surrounding material) such that the ultrasound signal is at least partially reflected at the boundary. At least a portion of the ultrasound signal is reflected back towards transducer 28. One or more electrical signals representing reflected ultrasound received at transducer 28 are sent from transducer 28 via a conduction pathway to the ultrasound console, for imaging and/or other data display to the physician. Simultaneously or subsequently transducer 28 continues to emit further ultrasound signals and the process is repeated, continuously in certain embodiments over a desired period of time.

Figure 4:
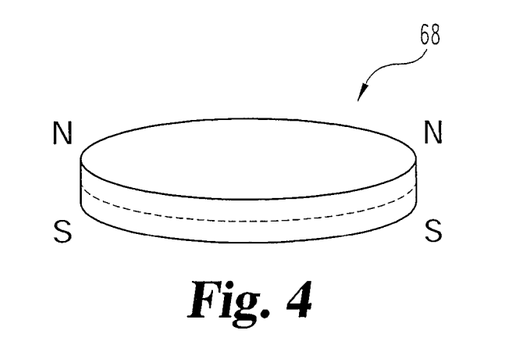
FIG. 4 is an illustrative perspective view of an alternate magnetic layer which could be used in the FIG. 1 embodiment.
Figure 5:
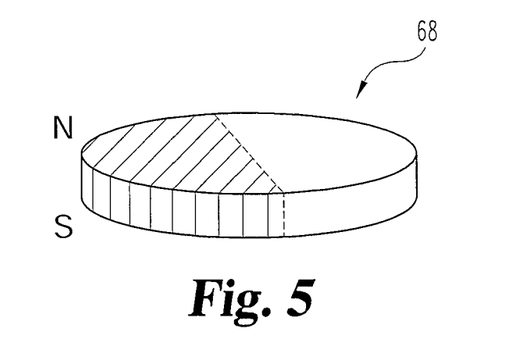
FIG. 5 is an illustrative perspective view of an alternate magnetic layer which could be used in the FIG. 1 embodiment.

Alternative embodiments include variations of pivot mechanism 30 and magnetic layer 68. In one embodiment, magnetic layer 68 is a disc-shaped permanent magnetic having poles aligned along an axis which is normal to the major surfaces of the disc (FIG. 4). In this embodiment, a magnetic field produced by coil 80 has a pole closest to magnetic layer 68 which repels the pole of magnetic layer 68 closest to coil 80. When coil 80 is energized, a repellant force creates a torque on pivot member 58 which causes it to rotate about the pivot axis. In other embodiments, magnetic layer 68 could be isolated to one half the circular disc in which the polls are aligned along an axis which is normal to the major surface of the disk (FIG. 5). In other embodiments, bias members 66 bias pivot member 58 to one or more other (non-forward-facing) neutral positions. In one example, in the neutral position the viewing angle of transducer 28 is perpendicular to the rotation axis, and a repulsion force from the magnetic fields causes pivot member 58 to rotate about the pivot axis toward the forward facing position (i.e. with transducer 28 viewing angle aligned with the rotation axis).

Figure 6:
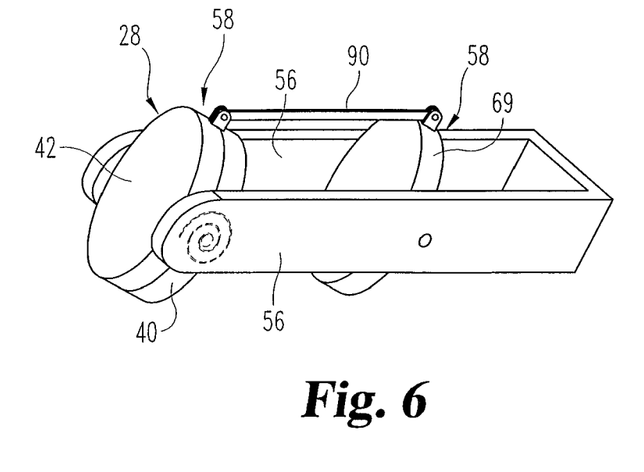
FIG. 6 is an illustrative perspective view of an embodiment of an alternate pivot mechanism.

In an alternative embodiment shown partially in FIG. 6, magnetic layer 69 is positioned on a separate, but parallel gimbal mount with a mechanical linkage 90 connecting transducer 28 to magnetic layer 69. The use of mechanical linkage 90 creates a four bar linkage between arms 56, magnetic layer 69, transducer 28, and mechanical linkage 90 with one degree of freedom, ensuring that transducer 28 pivots in parallel and responsive to pivoting rotation of magnetic layer 69 about a pivot axis.

Controls for motor 32 and/or coil 80 may be provided to maintain rotational motion of transducer 28 about the rotation axis and pivot axis at a particular rotational speed or pattern. For example, modalities such as a spin around the rotation axis of between 30-100 Hz may be combined with a slower pivoting around the pivot axis of about 1-2 Hz, to provide clear images forward and backward in a defined pattern. It has also been determined that a relatively slow spin around the rotation axis (e.g. about 1-2 Hz) combined with pivoting around the pivot axis more rapidly, e.g. near a resonant frequency of device 20 can provide good results. A modality providing a faster rotation around the rotation axis when transducer 28 is pointed closer to the rotation axis and slower rotation around the rotation axis when transducer 28 is further from the rotation axis is also useful for improving the image frame rate and clarity. Imaging continues, with adjustments to the positioning of transducer 28 and the ultrasound field, as the physician deems necessary or useful.

Device 20 facilitates capture of an image through a viewing window which is free from unnecessary acoustic attenuation such as artifacts, obstructions, or errors within the image. For example, positioning of transducer 28 at a location which is on an application side of motor 32 ensures that wires or other echogenic materials are not positioned within or across the viewing window of transducer 28, even as transducer 28 rotates in a full 360° rotation about the rotation axis as well as pivoting about the pivot axis. In this way, there are no wires or other reflecting materials which could cause artifacts within the image or block portions of the redirected ultrasound waves. This provides the physician a clear view of the entirety of the viewing window. As used herein, the term "window" includes a substantially obstruction-free pathway throughout the structure of device 20 between transducer 28 and organic fluids or tissue which may be positioned external to device 20 during use.

Device 20 is configured to be used with existing medical devices which are designed for percutaneous, intraluminal, or interstitial procedures. For example, device 20 can be used as or with a variety of catheters for different purposes, e.g. positioned on or within an application side of a catheter, depending on the particular configuration. Parts of device 20 as previously described can be positioned within an existing lumen within the catheter. In an alternative embodiment, device 20 could include an external casing (or sheath) which is similar to catheter 22 having walls 24 but being shortened so as to compactly contain device 20. Device 20 could be mounted externally to a catheter using a variety of mounting devices, glues or other types of arrangements. It will be understood by those skilled in the art that the particular type of mounting procedure for the device 20 to an existing medical device can include a variety of different types of mounting methods. Accordingly, the particular methods described herein are not indicative of any limiting aspects of the usage capabilities of the device 20.

In some embodiments described herein, hall sensors (not shown), optical encoders (not shown), ultrasound, back EMF, motor saliency, or a combination of one or more of these may be used to control and/or monitor angular positions of motor 32. It has been determined that hall sensors are advantageous as a feedback mechanism because of their small size and mature design. In some embodiments, the ultrasound beam or signals emitted and/or received by transducer 28 is used as a feedback mechanism to precisely assess or monitor the rotational position of motor 32 (and the ultrasound beam rotated by it) relative to the rest of device 20, ensuring proper registration of images obtained through transducer 28. Other features may be included with the embodiments noted herein such as indexing systems.

While some of the above discussion concerned specific use in the context of ultrasound system applications, it will be understood that embodiments of device 20 could also be used for a variety of other medical procedures and with a variety of other medical devices. The versatility of the embodiments described herein allows device 20 to be used to guide percutaneous therapeutic interventions such as, for example, embolism coils, stents, filters, graphs, balloons, biopsies, and ministering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the transducer. Device 20 can also be used to locate diseased tissue that will be treated or avoided. Device 20 can be used during a biopsy to provide an image of a needle being deployed into tissue. During a TIPS (transjugular intrahepatic portocaval shunt) procedure an image can be produced to allow a physician to watch a needle being placed into the portal vein. For AAA (aortic abdominal aneurysm) graft delivery, device 20 can allow a physician to place a guidewire into a contralateral leg. Device 20 could also be used to image the location of a deployed implantable device both during and after deployment.

Although particular materials were highlighted herein for some components of the device 20, those materials are not intended to be limiting of the types of materials which are suitable to be used in the device 20. Additionally, where materials were not highlighted, a variety of materials could be used such as certain types of metals, polymers, ceramics or other types of materials which are suitable for use in devices for small body cavity applications.

The device 20 could also be used for a variety of other medical procedures and with a variety of other medical devices. It will be understood by those skilled in the art that the particular type of mounting procedure can include a variety of different types of mounting methods. Accordingly, the particular methods described herein are not indicative of any limiting aspects of the usage capabilities of the device 20.

In the use of the terms "rotation" or "rotational," e.g. with respect to a rotational axis, it should be understood that even though rotation often implies an angle change much greater than 360°, the devices disclosed herein may be configured in certain embodiments so that the rotational angle may rotate through angles less than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angular change.

While the disclosure has been illustrated and described in detail in the drawings and foregoing description, the same is to be considered as illustrative and not restrictive in character, it being understood that only the preferred embodiments have been shown and described and that all changes, equivalents, and modifications that come within the spirit of the subject matter defined by following claims are desired to be protected. It will be understood that features or aspects described or indicated with a particular embodiment or structure may also be used with other features, aspects, structures or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical device comprising:
    a transducer for transmitting and/or receiving ultrasound signals;
    a motor operatively coupled with a drive shaft, wherein operation of the motor rotates the shaft about a rotation axis;
    a pivot mechanism operatively connected to the shaft, wherein the pivot mechanism rotates in response to rotation of the shaft, the pivot mechanism having a pivot member which is pivotable about at least one pivot axis, the pivot axis being substantially non-parallel to the rotation axis, the pivot member including a magnetic layer and the transducer; and
    a coil positioned concentric to and along the rotation axis between the motor and the transducer, wherein the coil includes a plurality of electrically conductive windings, and wherein application of electric current to the coil creates a torque on the pivot member about the pivot axis.

2. The device of claim 1, wherein the magnetic layer includes a diametric permanent magnet having a first magnetic field with poles aligned substantially perpendicular to the pivot axis, wherein application of electric current to the coil creates a second magnetic field with poles aligned substantially along the rotation axis, wherein interaction between the first and second magnetic fields creates the torque.

3. The device of claim 1, wherein the magnetic layer has poles aligned generally parallel with a transducer viewing angle, wherein application of electric current to the coil creates a second magnetic field with poles aligned along the rotation axis, and wherein interaction between the magnetic fields creates the torque.

4. The device of claim 1, wherein the coil is positioned concentrically outward of the drive shaft.

5. The device of claim 1, further comprising a bias member, wherein the bias member is positioned to apply a bias member force to the transducer which biases the transducer to a neutral position about the pivot axis and relative to the pivot mechanism.

6. The device of claim 5, wherein the torque is dependent upon the electric current to the coil, and wherein when the torque is insufficient to overcome the bias member force, the bias member force returns the transducer to the neutral position.

7. The device of claim 5, wherein the bias member is a conductor configured for carrying signals from the transducer.

8. The device of claim 1, wherein the rotation of the shaft about the rotation axis and the pivoting of the pivot member about the pivot axis are separably operable at one or more frequencies.

9. A method of operating the device of claim 8, comprising turning the motor faster when the pivot mechanism is in a state such that the ultrasound signals are pointing in a direction closer to the rotation axis, and turning the motor slower when the pivot mechanism is in a state such that the ultrasound signals are pointing in a direction further from the rotation axis.

10. The device of claim 1, further comprising a cylindrical sheath enclosing the motor and pivot mechanism, wherein the sheath provides structural support for the coil.

11. The device of claim 10, wherein the sheath is a catheter wall.

12. The device of claim 1, wherein the device is positioned within a catheter.

13. The device of claim 1, wherein the drive shaft includes a lumen extending therethrough.

14. The device of claim 1, further comprising a limit stop positioned to bound the pivotal motion of the pivot member at either end of its pivotal range.

15. The device of claim 14, further comprising two arms providing a mounting for the pivot member, wherein the limit stop is a bar extending between the two arms.

16. The device of claim 1, wherein the transducer is moveable throughout a range which defines a viewing window extending from the transducer, the device further comprising an opaque feature positioned within the viewing window, wherein the opaque feature provides angular positional information about the pivot member.

17. The device of claim 1, wherein the magnetic layer is positioned parallel to the transducer and pivotable about a second pivot axis, wherein the magnetic layer and transducer are connected such that the transducer pivots in response to pivotal motion of the magnetic layer.

18. The device of claim 1, further comprising a tubular member for housing the transducer, motor, and pivot mechanism, the tubular member having a distal chamber defined at least in part by a wall portion of the tubular member, the distal chamber housing at least the transducer and a medium, wherein the device is arranged for insertion into the body of a patient and the wall portion and the medium have similar ultrasound passage characteristics to the part of the body into which the tubular member is inserted, so that reflection of ultrasound at the boundary of the medium and the wall portion and at the boundary of the wall portion and body environment is reduced to a level acceptable for imaging through the boundary.

19. A medical device comprising:
    a transducer for transmitting and/or receiving ultrasound signals;
    a motor operatively coupled with a drive shaft, wherein operation of the motor rotates the shaft about a rotation axis;
    a pivot mechanism operatively connected to the shaft, wherein the pivot mechanism rotates in response to rotation of the shaft, the pivot mechanism having a pivot member which is pivotable about at least one pivot axis, the pivot axis being substantially non-parallel to the rotation axis, the pivot member including a magnetic layer and the transducer;
    a coil positioned concentric to and along the rotation axis between the motor and the transducer, wherein the coil includes a plurality of electrically conductive windings, and wherein application of electric current to the coil creates a torque on the pivot member about the pivot axis; and
    a bias member, wherein the bias member is positioned to apply a bias member force to the transducer which biases the transducer to a neutral position about the pivot axis and relative to the pivot mechanism;
    wherein the rotation of the shaft about the rotation axis and the pivoting of the pivot member about the pivot axis are separably operable at one or more frequencies.

20. The device of claim 19, further comprising a cylindrical sheath enclosing the motor and pivot mechanism, wherein the sheath provides structural support for the coil.

* * * * *